US012758241B2

(12) United States Patent
Taff et al.

(10) Patent No.: US 12,758,241 B2
(45) Date of Patent: Oct. 13, 2026

(54) TUBULAR THROMBECTOMY DEVICES

(71) Applicant: MAGNETO THROMBECTOMY SOLUTIONS LTD., Or Yehuda (IL)

(72) Inventors: Yuval Taff, Tel Aviv (IL); Gal Stern, Tel Aviv (IL); Itzhak Orion, Beer Sheva (IL)

(73) Assignee: Magneto Thrombectomy Solutions LTD, Or Yehuda (IL)

( * ) Notice: Subject to any disclaimer, the term of this patent is extended or adjusted under 35 U.S.C. 154(b) by 566 days.

(21) Appl. No.: 18/303,596

(22) Filed: Apr. 20, 2023

(65) Prior Publication Data

US 2023/0255653 A1 Aug. 17, 2023

Related U.S. Application Data

(63) Continuation of application No. 16/757,777, filed as application No. PCT/IB2018/058946 on Nov. 14, 2018, now Pat. No. 11,660,105.

(Continued)

(51) Int. Cl.
*A61B 17/22* (2006.01)
*A61B 17/00* (2006.01)

(52) U.S. Cl.
CPC .................. *A61B 17/22031* (2013.01); *A61B 2017/00831* (2013.01); *A61B 2017/22079* (2013.01); *A61B 2217/005* (2013.01)

(58) Field of Classification Search
CPC ........ A61B 2218/007; A61B 2217/005; A61B 2017/22079; A61B 2017/22034;

(Continued)

(56) References Cited

U.S. PATENT DOCUMENTS 4,027,674 A 6/1977 Tessler et al.
4,682,596 A 7/1987 Bales et al.

(Continued)

FOREIGN PATENT DOCUMENTS

CN 1209736 3/1997
CN 103732169 4/2014

(Continued)

OTHER PUBLICATIONS

U.S. Appl. No. 17/418,863 Office Action dated Feb. 29, 2024.

(Continued)

*Primary Examiner* — Jocelin C Tanner

(57) ABSTRACT

An apparatus for removing a blockage from a body includes a tube, configured to advance to the blockage, and a shaft configured to pass through the tube. The shaft includes one or more first electrodes, each of which constitutes part of a wall of the shaft or is wrapped around the wall, and one or more second electrodes, each of which constitutes part of the wall or is wrapped around the wall. One or more first electrically-conductive elements are configured to connect the first electrodes to a first terminal of a power source, and one or more second electrically-conductive elements are configured to connect the second electrodes to a second terminal of the power source. Each of the first electrodes is configured to attract the blockage when a voltage is applied by the power source between the first electrode and one of the second electrodes. Other embodiments are also described.

22 Claims, 6 Drawing Sheets

Related U.S. Application Data

(60) Provisional application No. 62/687,285, filed on Jun. 20, 2018, provisional application No. 62/590,296, filed on Nov. 23, 2017.

(58) Field of Classification Search
CPC A61B 2017/22002; A61B 2017/00831; A61B 18/1492; A61B 17/22031; A61B 17/22
USPC .......................................................... 606/127
See application file for complete search history.

(56) References Cited

U.S. PATENT DOCUMENTS

| | | | |
|---|---|---|---|
| 5,122,136 | A | 6/1992 | Guglielmi et al. |
| 5,125,928 | A | 6/1992 | Parins et al. |
| 5,300,068 | A | 4/1994 | Rosar et al. |
| 5,354,295 | A | 10/1994 | Guglielimi et al. |
| 5,433,708 | A | 7/1995 | Nichols et al. |
| 5,449,357 | A | 9/1995 | Zinnanti |
| 5,507,743 | A | 4/1996 | Edwards et al. |
| 5,545,193 | A | 8/1996 | Fleischman et al. |
| 5,569,204 | A | 10/1996 | Cramer |
| 5,603,731 | A | 2/1997 | Whitney |
| 5,722,401 | A | 3/1998 | Pietroski et al. |
| 5,827,278 | A | 10/1998 | Webster, Jr. |
| 5,851,206 | A | 12/1998 | Guglielmi et al. |
| 5,876,398 | A | 3/1999 | Mulier et al. |
| 5,913,854 | A | 6/1999 | Maguire et al. |
| 5,925,042 | A | 7/1999 | Gough et al. |
| 6,013,076 | A | 1/2000 | Goble et al. |
| 6,047,700 | A | 4/2000 | Eggers et al. |
| 6,179,824 | B1 | 1/2001 | Eggers et al. |
| 6,190,381 | B1 | 2/2001 | Olsen et al. |
| 6,210,404 | B1 | 4/2001 | Shadduck et al. |
| 6,228,109 | B1 | 5/2001 | Tu et al. |
| 6,248,113 | B1 * | 6/2001 | Fina ..................... A61B 17/221 606/127 |
| 6,322,559 | B1 | 11/2001 | Daulton et al. |
| 6,344,041 | B1 | 2/2002 | Kupiecki et al. |
| 6,397,850 | B1 | 6/2002 | Scheldrup et al. |
| 6,554,827 | B2 | 4/2003 | Chandrasekaran et al. |
| 6,582,423 | B1 | 6/2003 | Thapliyal et al. |
| 6,658,288 | B1 | 12/2003 | Hayashi |
| 6,730,104 | B1 | 5/2004 | Sepetka et al. |
| 6,855,143 | B2 | 2/2005 | Davison et al. |
| 7,077,842 | B1 | 7/2006 | Cosman |
| 8,197,478 | B2 | 6/2012 | Hayashi et al. |
| 8,473,029 | B2 | 6/2013 | Gerhart et al. |
| 8,579,893 | B2 | 11/2013 | Hoey |
| 8,747,416 | B2 | 6/2014 | Hakala et al. |
| 8,814,859 | B2 | 8/2014 | Drasler et al. |
| 8,968,304 | B2 | 3/2015 | Katou |
| 9,795,400 | B2 | 10/2017 | Davidson |
| 10,265,515 | B2 | 4/2019 | Davidson |
| 10,434,295 | B2 | 10/2019 | Stigall et al. |
| 10,499,939 | B2 | 12/2019 | Davidson |
| 10,709,463 | B2 | 7/2020 | Girdhar et al. |
| 10,716,610 | B2 | 7/2020 | Yamanishi et al. |
| 10,758,303 | B2 | 9/2020 | Xiao et al. |
| 10,874,410 | B2 | 12/2020 | Scarpine et al. |
| 10,874,411 | B2 | 12/2020 | Nguyen et al. |
| 10,912,608 | B2 | 2/2021 | Lam et al. |
| 10,987,117 | B2 | 4/2021 | Girdhar et al. |
| 11,058,444 | B2 | 7/2021 | Girdhar et al. |
| 11,090,071 | B2 | 8/2021 | Girdhar et al. |
| 11,160,571 | B2 | 11/2021 | Nguyen et al. |
| 11,191,558 | B2 | 12/2021 | Nguyen et al. |
| 11,317,931 | B2 | 5/2022 | Davidson |
| 11,395,668 | B2 | 7/2022 | Girdhar et al. |
| 11,523,838 | B2 | 12/2022 | Nguyen et al. |
| 11,633,201 | B2 | 4/2023 | Girdhar et al. |
| 11,666,350 | B2 | 6/2023 | Nguyen et al. |
| 2001/0001314 | A1 | 5/2001 | Davison et al. |
| 2002/0058937 | A1 | 5/2002 | Maltese |
| 2002/0072740 | A1 | 6/2002 | Chandrasekaran et al. |
| 2002/0072764 | A1 | 6/2002 | Sepetka et al. |
| 2002/0133111 | A1 | 9/2002 | Shadduck |
| 2003/0045870 | A1 | 3/2003 | Madsen |
| 2003/0050634 | A1 | 3/2003 | Ellman et al. |
| 2003/0125787 | A1 | 7/2003 | Shchervinsky et al. |
| 2003/0130571 | A1 | 7/2003 | Lattouf |
| 2004/0073243 | A1 | 4/2004 | Sepetka et al. |
| 2004/0082948 | A1 | 4/2004 | Stewart et al. |
| 2005/0159739 | A1 | 7/2005 | Paul et al. |
| 2005/0251134 | A1 | 11/2005 | Woloszko et al. |
| 2006/0058838 | A1 | 3/2006 | Bose et al. |
| 2006/0089638 | A1 | 4/2006 | Carmel et al. |
| 2006/0195137 | A1 | 8/2006 | Sepetka et al. |
| 2006/0224155 | A1 | 10/2006 | Schmaltz |
| 2007/0027448 | A1 | 2/2007 | Paul et al. |
| 2007/0078457 | A1 | 4/2007 | Paul et al. |
| 2007/0156082 | A1 | 7/2007 | Scherman |
| 2007/0156130 | A1 | 7/2007 | Thistle |
| 2007/0255270 | A1 | 11/2007 | Carney |
| 2008/0161796 | A1 | 7/2008 | Cao et al. |
| 2008/0161803 | A1 | 7/2008 | Oral et al. |
| 2008/0161893 | A1 | 7/2008 | Paul et al. |
| 2008/0262489 | A1 | 10/2008 | Steinke |
| 2009/0240250 | A1 | 9/2009 | Hayashi et al. |
| 2009/0248012 | A1 | 10/2009 | Maor et al. |
| 2010/0092939 | A1 | 4/2010 | Belous et al. |
| 2010/0114017 | A1 | 5/2010 | Lenker et al. |
| 2010/0312223 | A1 | 12/2010 | Kozak et al. |
| 2011/0022045 | A1 | 1/2011 | Cao et al. |
| 2011/0144639 | A1 | 6/2011 | Govari |
| 2011/0218528 | A1 | 9/2011 | Ogata et al. |
| 2011/0257649 | A1 | 10/2011 | Geistert et al. |
| 2011/0288541 | A1 | 11/2011 | Faure |
| 2011/0301594 | A1 * | 12/2011 | Orion ................. A61B 18/1492 606/41 |
| 2011/0308527 | A1 | 12/2011 | Harrington et al. |
| 2012/0130169 | A1 | 5/2012 | Mesallum |
| 2012/0232374 | A1 | 9/2012 | Werneth et al. |
| 2012/0239022 | A1 | 9/2012 | Wolfe |
| 2012/0296262 | A1 | 11/2012 | Ogata et al. |
| 2013/0090644 | A1 | 4/2013 | Williams et al. |
| 2013/0123872 | A1 | 5/2013 | Bornzin et al. |
| 2013/0310823 | A1 | 11/2013 | Gelfand et al. |
| 2013/0325003 | A1 | 12/2013 | Kapur et al. |
| 2013/0325041 | A1 | 12/2013 | Annest et al. |
| 2014/0052147 | A1 | 2/2014 | Hakala et al. |
| 2014/0074113 | A1 | 3/2014 | Hakala et al. |
| 2014/0155931 | A1 | 6/2014 | Bose et al. |
| 2014/0276748 | A1 | 9/2014 | Ku et al. |
| 2014/0276913 | A1 | 9/2014 | Tah et al. |
| 2014/0277013 | A1 | 9/2014 | Sepetka et al. |
| 2014/0309579 | A1 | 10/2014 | Rubinsky et al. |
| 2014/0364896 | A1 | 12/2014 | Consigny |
| 2015/0005792 | A1 | 1/2015 | Ahn |
| 2015/0038963 | A1 | 2/2015 | Panos et al. |
| 2015/0133990 | A1 | 5/2015 | Davidson |
| 2015/0133998 | A1 | 5/2015 | Cohen et al. |
| 2015/0305756 | A1 | 10/2015 | Rosenbluth et al. |
| 2016/0008014 | A1 | 1/2016 | Rosenbluth et al. |
| 2016/0066989 | A1 | 3/2016 | Davies et al. |
| 2016/0166266 | A1 | 6/2016 | Nita |
| 2016/0287276 | A1 | 10/2016 | Cox et al. |
| 2017/0014272 | A1 | 1/2017 | Ray et al. |
| 2017/0079672 | A1 | 3/2017 | Quick et al. |
| 2017/0105745 | A1 | 4/2017 | Rosenbluth et al. |
| 2017/0112514 | A1 | 4/2017 | Marchand et al. |
| 2017/0172648 | A1 | 6/2017 | Germain et al. |
| 2017/0189041 | A1 | 7/2017 | Cox et al. |
| 2017/0265878 | A1 | 9/2017 | Marchand et al. |
| 2017/0348049 | A1 | 12/2017 | Vrba et al. |
| 2018/0092652 | A1 | 4/2018 | Marchand et al. |
| 2018/0116717 | A1 | 5/2018 | Taff et al. |
| 2018/0161085 | A1 | 6/2018 | Shin et al. |
| 2018/0296240 | A1 | 10/2018 | Rosenbluth et al. |
| 2018/0353194 | A1 | 12/2018 | Shaffer et al. |
| 2018/0361116 | A1 | 12/2018 | Quick et al. |
| 2019/0046219 | A1 | 2/2019 | Marchand et al. |
| 2019/0070401 | A1 | 3/2019 | Merritt et al. |
| 2019/0142452 | A1 | 5/2019 | Trosper et al. |

(56) References Cited

U.S. PATENT DOCUMENTS

| | | | |
|---|---|---|---|
| 2019/0150959 | A1 | 5/2019 | Cox et al. |
| 2019/0231373 | A1 | 8/2019 | Quick et al. |
| 2019/0262069 | A1 | 8/2019 | Taff et al. |
| 2019/0321071 | A1 | 10/2019 | Marchand et al. |
| 2019/0380651 | A1 | 12/2019 | Carreel et al. |
| 2019/0388111 | A1 | 12/2019 | Nguyen et al. |
| 2019/0388112 | A1 | 12/2019 | Nguyen et al. |
| 2020/0170666 | A1 | 6/2020 | Trosper et al. |
| 2021/0267612 | A1 | 9/2021 | Girdhar et al. |
| 2021/0353323 | A1 | 11/2021 | Teigen et al. |
| 2021/0361314 | A1 | 11/2021 | Teigen et al. |
| 2022/0015798 | A1 | 1/2022 | Marchand et al. |
| 2022/0022900 | A1 | 1/2022 | Nguyen et al. |
| 2022/0071697 | A1 | 3/2022 | Taff et al. |
| 2022/0125455 | A1 | 4/2022 | Girdhar et al. |
| 2022/0211429 | A1 | 7/2022 | Taff et al. |
| 2022/0218372 | A1 | 7/2022 | Nguyen et al. |
| 2022/0218373 | A1 | 7/2022 | Davidson |
| 2022/0387051 | A1 | 12/2022 | Girdhar et al. |
| 2023/0064470 | A1 | 3/2023 | Girdhar et al. |
| 2023/0113257 | A1 | 4/2023 | Nguyen et al. |

FOREIGN PATENT DOCUMENTS

| | | |
|---|---|---|
| CN | 104207844 | 12/2014 |
| CN | 104224318 | 12/2014 |
| DE | 102010014778 | 10/2011 |
| EP | 1329196 | 7/2003 |
| EP | 1602338 | 12/2005 |
| EP | 1980200 | 10/2008 |
| EP | 2359764 | 8/2011 |
| JP | 06-63060 | 3/1994 |
| JP | H09-501328 | 2/1997 |
| JP | 10-57392 | 3/1998 |
| JP | H10-57392 | 3/1998 |
| JP | 2016-511126 | 4/2016 |
| WO | WO 94/26228 | 11/1994 |
| WO | WO 97/724993 | 7/1997 |
| WO | WO 00/62851 | 10/2000 |
| WO | WO 01/24720 | 4/2001 |
| WO | WO 2010/061376 | 6/2010 |
| WO | WO 2014/025397 | 2/2014 |
| WO | WO 2014/151123 | 9/2014 |
| WO | WO 2015/074032 | 5/2015 |
| WO | WO 2015/076864 | 5/2015 |
| WO | WO 2018/127796 | 7/2018 |
| WO | WO 2018/172891 | 9/2018 |
| WO | WO 2019/102307 | 5/2019 |
| WO | WO 2019/243992 | 12/2019 |

OTHER PUBLICATIONS

International Preliminary Report on Patentability Dated Jun. 4, 2020 From the International Bureau of WIPO Re. Application No. PCT/IB2018/058946. (7 Pages).

International Preliminary Report on Patentability Dated Sep. 30, 2020 From the International Bureau of WIPO Re. Application No. PCT/IB2019/055032. (9 Pages).

International Search Report and the Written Opinion Dated Feb. 21, 2019 From the International Searching Authority Re. Application No. PCT/IB2018/058946. (8 Pages).

International Search Report and the Written Opinion Dated Oct. 28, 2019 From the International Searching Authority Re. Application No. PCT/IB2019/055032. (32 Pages).

Supplementary European Search Report and the European Search Opinion Dated Mar. 4, 2022 From the European Patent Office Re. Application No. 810005. (6 Pages).

Communication Pursuant to Article 94(3) EPC Dated Feb. 10, 2022 From the European Patent Office Re. Application No. 18880491.8. (3 Pages).

Supplementary European Search Report and the European Search Opinion Dated Jun. 23, 2021 From the European Patent Office Re. Application No. 18880491.8. (5 Pages).

Gross et al., "Dump the pump: manual aspiration thrombectomy (MAT) with a syringe is technically effective, expeditious, and cost-efficient," Journal of NeuroInterventional Surgery, vol. 10, No. 4, pp. 1-4, year 2017.

U.S. Appl. No. 17/052,813 Office Action dated Jan. 11, 2024.

EP Application # 18772459.6 Office Action dated Dec. 13, 2023.

EP Application # 18736539.0 Office Action dated Dec. 14, 2023.

CA Application # 3055267 Office Action dated Oct. 23, 2023.

Advisory Action Before the Filing of An Appeal Brief Dated Sep. 21, 2017 From the US Patent and Trademark Office Re. U.S. Appl. No. 13/127,118. (5 Pages).

Applicant-Initiated Interview Summary Dated Mar. 7, 2017 From the US Patent and Trademark Office Re. U.S. Appl. No. 13/127,118. (10 Pages).

Applicant-Initiated Interview Summary Dated Sep. 14, 2016 From the US Patent and Trademark Office Re. U.S. Appl. No. 13/127,118. (14 Pages).

Applicant-Initiated Interview Summary Dated Aug. 24, 2017 From the US Patent and Trademark Office Re. U.S. Appl. No. 13/127,118. (13 Pages).

Communication Pursuant to Article 94(3) EPC Dated Dec. 7, 2018 From the European Patent Office Re. Application No. 17151631.3. (4 Pages).

Corrected Notice of Allowability Dated May 2, 2018 From the US Patent and Trademark Office Re. U.S. Appl. No. 13/127,118. (6 Pages).

Corrected Notice of Allowability Dated Jun. 27, 2018 From the US Patent and Trademark Office Re. U.S. Appl. No. 13/127,118. (7 Pages).

European Search Report and the European Search Opinion Dated May 22, 2017 From the European Patent Office Re. Application No. 17151631.3. (7 Pages).

International Preliminary Report on Patentability Dated May 12, 2011 From the International Bureau of WIPO Re. Application No. PCT/IL2009/001024. (7 Pages).

International Preliminary Report on Patentability Dated Jul. 18, 2019 From the International Bureau of WIPO Re. Application No. PCT/IB2018/050010. (8 Pages).

International Search Report and the Written Opinion Dated Apr. 5, 2010 From the International Searching Authority Re. Application No. PCT/IL2009/001024. (9 Pages).

International Search Report and the Written Opinion Dated May 10, 2018 From the International Searching Authority Re. Application No. PCT/IB2018/050010. (28 Pages).

International Search Report and the Written Opinion Dated May 31, 2020 From the International Searching Authority Re. Application No. PCT/IB2020/051418. (15 Pages).

Notice of Allowance Dated Jan. 25, 2023 From the US Patent and Trademark Office Re. U.S. Appl. No. 16/757,777. (9 Pages).

Notice of Allowance Dated May 15, 2018 From the US Patent and Trademark Office Re. U.S. Appl. No. 13/127,118. (6 Pages).

Notice of Allowance Dated Mar. 19, 2018 From the US Patent and Trademark Office Re. U.S. Appl. No. 13/127,118. (21 Pages).

Notice of Reasons for Refusal Dated Mar. 7, 2023 From the Japan Patent Office Re. Application No. 2022-002663 and Its Translation Into English. (9 Pages).

Notification of Office Action and Search Report Dated Jun. 2, 2021 From the State Intellectual Property Office of the People's Republic of China Re. Application No. 201880005449.3 (7 Pages).

Notification of Office Action and Search Report Dated Nov. 9, 2021 From the State Intellectual Property Office of the People's Republic of China Re. Application No. 201880005449.3 (7 Pages).

Notification of Office Action and Search Report Dated Apr. 24, 2022 From the State Intellectual Property Office of the People's Republic of China Re. Application No. 201880017216.5 and Its Translation Into English. (14 Pages).

Office Action Dated Jun. 8, 2017 From the US Patent and Trademark Office Re. U.S. Appl. No. 13/127,118. (20 Pages).

Office Action Dated Jan. 13, 2015 From the US Patent and Trademark Office Re. U.S. Appl. No. 13/127,118. (24 Pages).

Office Action Dated Apr. 22, 2014 From the US Patent and Trademark Office Re. U.S. Appl. No. 13/127,118. (33 Pages).

(56) References Cited

OTHER PUBLICATIONS

Office Action Dated May 24, 2016 From the US Patent and Trademark Office Re. U.S. Appl. No. 13/127,118. (21 Pages).
Official Action Dated Dec. 7, 2021 From the US Patent and Trademark Office Re. U.S. Appl. No. 16/381,014. (13 Pages).
Official Action Dated Aug. 11, 2015 From the US Patent and Trademark Office Re. U.S. Appl. No. 13/127,118. (24 Pages).
Official Action Dated Jan. 12, 2017 From the US Patent and Trademark Office Re. U.S. Appl. No. 13/127,118. (16 Pages).
Official Action Dated Feb. 17, 2022 From the US Patent and Trademark Office Re. U.S. Appl. No. 16/381,014. (11 Pages).
Official Action Dated Oct. 18, 2021 From the US Patent and Trademark Office Re. U.S. Appl. No. 15/859,776. (11 Pages).
Official Action Dated May 19, 2021 From the US Patent and Trademark Office Re. U.S. Appl. No. 15/859,776. (14 Pages).
Official Action Dated Jul. 27, 2021 From the US Patent and Trademark Office Re. U.S. Appl. No. 15/859,776. (12 Pages).
Official Action Dated Mar. 27, 2025 from the US Patent and Trademark Office Re. U.S. Appl. No. 17/700,575. (55 pages).
Official Action Dated Sep. 28, 2022 From the US Patent and Trademark Office Re. U.S. Appl. No. 16/757,777. (41 Pages).
Official Action Dated Jan. 29, 2021 From the US Patent and Trademark Office Re. U.S. Appl. No. 15/859,776. (15 Pages).
Patent Examination Report Dated May 8, 2020 From the Australian Government, IP Australia Re. Application No. 2018206023. (9 Pages).
Patent Examination Report Dated Nov. 29, 2019 From the Australian Government, IP Australia Re. Application No. 2018206023. (4 Pages).
Requisition by the Examiner Dated Apr. 24, 2024 From the Innovation, Science and Economic Development Canada, Canadian Intellectual Property Office Re. Application No. 3,046,758. (5 Pages).
Restriction OA Dated Aug. 8, 2022 From the US Patent and Trademark Office Re. U.S. Appl. No. 16/757,777. (6 Pages).
Supplementary European Search Report and the European Search Opinion Dated Jul. 3, 2020 From the European Patent Office Re. Application No. 118736539.0. (7 Pages).
Gralla et al. "A Dedicated Animal Model for Mechanical Thrombectomy in Acute Stroke", American journal of Neuroradiology, 27(6): 1357-1361, Jun. 2006.
Sawyer et al. "Electrical Hemostasis in Uncontrollable Bleeding States", Annals of Surgery, 154(4): 556-562, Oct. 1961.

* cited by examiner

TUBULAR THROMBECTOMY DEVICES

CROSS-REFERENCE TO RELATED APPLICATIONS

The present application is a continuation of U.S. application Ser. No. 16/757,777, which was filed on Apr. 21, 2020 in the national phase of International Application PCT/IB2018/058946, which was filed on Nov. 14, 2018 and claims the benefit of U.S. Provisional Application 62/590,296, entitled "Variety of electric thrombectomy devices and methods," filed Nov. 23, 2017, and U.S. Provisional Application 62/687,285, entitled "Various thrombectomy devices," filed Jun. 20, 2018. The respective disclosures of the aforementioned references are incorporated herein by reference.

FIELD OF THE INVENTION

The present invention relates generally to medical devices and procedures, such as thrombectomy procedures for the removal of thrombi from blood vessels.

BACKGROUND

U.S. Pat. No. 10,028,782 to Orion describes a flexible catheter device capable of being introduced into a body passage and withdrawing fluids therefrom or introducing fluids thereinto. The device includes electrodes configured to apply electrical signals in the body passage for carrying out thrombus dissolution and/or thrombectomy, wherein one of said electrodes is designed to contact the thrombus material and remove it or dissolve it, and wherein the electrical voltage signals are unipolar pulsatile voltage signals.

U.S. Patent Application Publication 2018/0116717 to Taff et al. describes an apparatus for removal of a thrombus from a body of a subject. The apparatus includes a first electrode, made of a first conductive metal, a second electrode, made of a second conductive metal that is different from the first conductive metal, and a voltage source, configured to apply a positive unipolar voltage between the first electrode and the second electrode while the first electrode is in contact with the thrombus, and while the second electrode is inside the body of the subject.

International Patent Application Publication WO/2018/172891 to Taff et al. describes an apparatus that includes an electrically-insulating tube, which includes a distal end having a circumferential wall that is shaped to define one or more perforations, configured for insertion into a body of a subject, an outer electrode, disposed over the distal end of the electrically-insulating tube, and configured to lie at least partly within a thrombus while the electrically-insulating tube is inside the body, and an inner electrode, configured to lie, within the tube, opposite the perforations, while the outer electrode lies at least partly within the thrombus. The outer electrode is configured to attract the thrombus while the outer electrode lies at least partly within the thrombus and the inner electrode lies opposite the perforations, when a positive voltage is applied between the outer electrode and the inner electrode such that electric current flows through the perforations.

SUMMARY OF THE INVENTION

There is provided, in accordance with some embodiments of the present invention, an apparatus for removing a blockage from a body of a subject. The apparatus includes a tube, configured to advance to the blockage, and including a proximal hub configured to connect to a suction-applying device such that, following the advancement of the tube to the blockage, a suction force generated by the suction-applying device is applied, via the tube, to the blockage. The apparatus further includes a shaft, including a first electrically-conductive circumferential portion and a second electrically-conductive circumferential portion, configured to pass through the tube. The apparatus further includes a first electrically-conductive element, configured to connect the first electrically-conductive circumferential portion to a first terminal of a power source, and a second electrically-conductive element, configured to connect the second electrically-conductive circumferential portion to a second terminal of the power source. The first electrically-conductive circumferential portion is configured to attract the blockage when a voltage is applied by the power source, via the first electrically-conductive element and the second electrically-conductive element, between the first electrically-conductive circumferential portion and the second electrically-conductive circumferential portion, such that the blockage is anchored to the shaft while the suction force is applied to the blockage.

In some embodiments, the second electrically-conductive circumferential portion is disposed proximally to the first electrically-conductive circumferential portion.

In some embodiments, the first electrically-conductive circumferential portion of the shaft is disposed at a distal end of the shaft.

In some embodiments, the first electrically-conductive element runs through the shaft from a proximal end of the shaft to the first electrically-conductive circumferential portion.

In some embodiments, the shaft is fixed to an inner wall of the tube.

In some embodiments, the shaft is configured to move axially through the tube.

In some embodiments, an outer diameter of the first electrically-conductive circumferential portion of the shaft is greater than a maximum outer diameter of a remainder of the shaft.

In some embodiments, the outer diameter of the first electrically-conductive circumferential portion of the shaft is at least 30% larger than the maximum outer diameter.

In some embodiments, the outer diameter of the first electrically-conductive circumferential portion of the shaft is at least twice as large as the maximum outer diameter.

In some embodiments, a length of the first electrically-conductive circumferential portion of the shaft is at least 5 mm.

In some embodiments, an outer diameter of the first electrically-conductive circumferential portion of the shaft is greater than 0.25 mm.

In some embodiments, the outer diameter is greater than 0.5 mm.

In some embodiments, an inner diameter of the tube is greater than 0.7 mm.

In some embodiments, the first electrically-conductive circumferential portion of the shaft is not expandable.

There is further provided, in accordance with some embodiments of the present invention, a method for removing a blockage from a body of a subject. The method includes advancing a tube to the blockage and, subsequently to advancing the tube, applying a voltage between a first electrically-conductive circumferential portion of a shaft, which protrudes distally from the tube, and a second electrically-conductive circumferential portion of the shaft, such that the first electrically-conductive circumferential portion attracts the blockage. The method further includes, subsequently to beginning to apply the voltage, applying a suction force, via the tube, to the blockage, and, while applying the suction force, withdrawing the tube and the shaft from the body of the subject.

In some embodiments, the method further includes, prior to applying the voltage, advancing the shaft from the tube, such that the first electrically-conductive circumferential portion of the shaft protrudes distally from the tube.

In some embodiments, the blockage is located within a blood vessel of the subject, and advancing the tube includes advancing the tube through vasculature of the subject.

In some embodiments, withdrawing the tube and the shaft from the body of the subject includes, prior to withdrawing the tube from the body of the subject, continually ascertaining that the suction force is aspirating fluid through the tube and, in response thereto, withdrawing the shaft through the tube.

In some embodiments, applying the voltage includes applying a positive unipolar voltage.

There is further provided, in accordance with some embodiments of the present invention, an apparatus for removing a blockage from a body of a subject. The apparatus includes a hollow shaft having an open distal end and including a first electrically-conductive circumferential portion and a second electrically-conductive circumferential portion. The apparatus further includes a first electrically-conductive element, configured to connect the first electrically-conductive circumferential portion to a first terminal of a power source, and a second electrically-conductive element, configured to connect the second electrically-conductive circumferential portion to a second terminal of the power source. The first electrically-conductive circumferential portion is configured to attract the blockage when a voltage is applied by the power source, via the first electrically-conductive element and the second electrically-conductive element, between the first electrically-conductive circumferential portion and the second electrically-conductive circumferential portion.

In some embodiments, the second electrically-conductive circumferential portion is disposed proximally to the first electrically-conductive circumferential portion.

In some embodiments, the first electrically-conductive element runs through the shaft from a proximal end of the shaft to the first electrically-conductive circumferential portion.

In some embodiments, the second electrically-conductive element runs through the shaft from a proximal end of the shaft to the second electrically-conductive circumferential portion.

In some embodiments, the first electrically-conductive element runs along an inner wall of the shaft.

In some embodiments, the first electrically-conductive element is coiled along the inner wall of the shaft.

In some embodiments, the first electrically-conductive element runs between an inner wall of the shaft and an outer wall of the shaft.

In some embodiments, the first electrically-conductive element is coiled between the inner wall and the outer wall.

In some embodiments, an inner diameter of the shaft is at least 0.3 mm.

In some embodiments, an outer diameter of the first electrically-conductive circumferential portion is at least 0.7 mm.

In some embodiments, a length of the first electrically-conductive circumferential portion is at least 5 mm.

In some embodiments, the shaft includes a proximal hub configured to connect to a suction-applying device.

There is further provided, in accordance with some embodiments of the present invention, a method for removing a blockage from a body of a subject. The method includes advancing a hollow shaft, which has an open distal end, to the blockage. The method further includes, subsequently to advancing the shaft, applying a voltage between a first electrically-conductive circumferential portion of the shaft and a second electrically-conductive circumferential portion of the shaft, such that the first electrically-conductive circumferential portion attracts the blockage. The method further includes, subsequently to beginning to apply the voltage, withdrawing the shaft from the body of the subject while aspirating debris through the open distal end of the shaft.

In some embodiments, the blockage is located within a blood vessel of the subject, and advancing the hollow shaft includes advancing the hollow shaft through vasculature of the subject.

In some embodiments, applying the voltage includes applying a positive unipolar voltage.

There is further provided, in accordance with some embodiments of the present invention, a method for removing a blockage from a body of a subject. The method includes advancing a hollow shaft having an open distal end, over a guidewire, to the blockage. The method further includes, subsequently to advancing the shaft, applying a voltage between a first electrically-conductive circumferential portion of the shaft and a second electrically-conductive circumferential portion of the shaft, such that the first electrically-conductive circumferential portion attracts the blockage. The method further includes, subsequently to beginning to apply the voltage, withdrawing the shaft from the body of the subject.

In some embodiments, the blockage is located within a blood vessel of the subject, and advancing the hollow shaft includes advancing the hollow shaft through vasculature of the subject.

In some embodiments, applying the voltage includes applying a positive unipolar voltage.

There is further provided, in accordance with some embodiments of the present invention, a method for removing a blockage from a body of a subject. The method includes advancing a hollow shaft, which has an open distal end, to the blockage. The method further includes, subsequently to advancing the shaft, applying a voltage between a first electrically-conductive circumferential portion of the shaft and a second electrically-conductive circumferential portion of the shaft, such that the first electrically-conductive circumferential portion attracts the blockage. The method further includes passing a tool through the open distal end of the shaft and into the body of the subject, and, subsequently to beginning to apply the voltage, withdrawing the shaft and the tool from the body of the subject while catching fragments of the blockage with the tool.

In some embodiments, the blockage is located within a blood vessel of the subject, and advancing the hollow shaft includes advancing the hollow shaft through vasculature of the subject.

In some embodiments, applying the voltage includes applying a positive unipolar voltage.

There is further provided, in accordance with some embodiments of the present invention, an apparatus for removing a blockage from a body of a subject. The apparatus includes a shaft, including a plurality of first electrically-conductive circumferential portions and one or more second electrically-conductive circumferential portions. The apparatus further includes one or more first electrically-conductive elements, which run through the shaft from a proximal end of the shaft to the first electrically-conductive circumferential portions, and are configured to connect the first electrically-conductive circumferential portions to a first terminal of a power source. The apparatus further includes one or more second electrically-conductive elements, which run through the shaft from the proximal end of the shaft to the second electrically-conductive circumferential portions, and are configured to connect the second electrically-conductive circumferential portions to a second terminal of the power source. Each of the first electrically-conductive circumferential portions is configured to attract the blockage when a voltage is applied by the power source, via one of the first electrically-conductive elements and one of the second electrically-conductive elements, between the first electrically-conductive circumferential portion and one of the second electrically-conductive circumferential portions.

In some embodiments, the first electrically-conductive elements include multiple first electrically-conductive elements that run to at least some of the first electrically-conductive circumferential portions, respectively.

In some embodiments, the apparatus further includes one or more interconnecting electrically-conductive elements that interconnect at least some of the first electrically-conductive circumferential portions.

In some embodiments, the shaft includes:

a distal pair of electrically-conductive circumferential portions, including one of the first electrically-conductive circumferential portions and one of the second electrically-conductive circumferential portions; and a more proximal pair of electrically-conductive circumferential portions, disposed proximally to the distal pair, including another one of the first electrically-conductive circumferential portions and another one of the second electrically-conductive circumferential portions.

In some embodiments, in each of the distal pair and the proximal pair, the second electrically-conductive circumferential portion is disposed proximally to the first electrically-conductive circumferential portion.

In some embodiments, the second electrically-conductive circumferential portions are disposed between successive pairs of the first electrically-conductive circumferential portions, respectively.

In some embodiments, the shaft includes at least one triad of electrically-conductive circumferential portions, each triad including two of the first electrically-conductive circumferential portions that are disposed distally and proximally, respectively, to one of the second electrically-conductive circumferential portions.

In some embodiments, a distance between each of the first electrically-conductive circumferential portions and a nearest one of the second electrically-conductive circumferential portions is less than 10 mm.

In some embodiments, the distance is less than 3 mm.

There is further provided, in accordance with some embodiments of the present invention, an apparatus for removing a blockage from a body of a subject. The apparatus includes a shaft, including a plurality of electrically-conductive circumferential portions. The apparatus further includes one or more first electrically-conductive elements, which run through the shaft from a proximal end of the shaft to the first electrically-conductive circumferential portions, and are configured to connect the first electrically-conductive circumferential portions to a first terminal of a power source. The apparatus further includes a second electrically-conductive element, configured to run through the shaft and to proximally connect to a second terminal of the power source. Each of the first electrically-conductive circumferential portions is configured to attract the blockage when a voltage is applied by the power source, via one of the first electrically-conductive elements, between the first electrically-conductive circumferential portion and the second electrically-conductive element.

In some embodiments, the first electrically-conductive elements include multiple first electrically-conductive elements that run to at least some of the first electrically-conductive circumferential portions, respectively.

In some embodiments, the apparatus further includes one or more interconnecting electrically-conductive elements that interconnect at least some of the first electrically-conductive circumferential portions.

In some embodiments, the first electrically-conductive elements run along an inner wall of the shaft.

In some embodiments, the first electrically-conductive elements are coiled along the inner wall of the shaft.

In some embodiments, the shaft includes an electrically-insulative perforated layer attached to the inner wall of the shaft, and the first electrically-conductive elements run between the inner wall of the shaft and the perforated layer.

There is further provided, in accordance with some embodiments of the present invention, a method for removing a blockage from a body of a subject. The method includes advancing a shaft, which includes a plurality of electrically-conductive circumferential portions, to the blockage. The method further includes, subsequently to advancing the shaft, applying a voltage between two or more of the electrically-conductive circumferential portions of the shaft and at least one reference electrode, such that the two or more of the electrically-conductive circumferential portions attract the blockage. The method further includes, subsequently to beginning to apply the voltage, withdrawing the shaft from the body of the subject.

In some embodiments, the blockage is located within a blood vessel of the subject, and advancing the shaft includes advancing the shaft through vasculature of the subject.

In some embodiments, applying the voltage includes applying a positive unipolar voltage.

There is further provided, in accordance with some embodiments of the present invention, a method for removing a blockage from a body of a subject. The method includes advancing a shaft, which includes a plurality of electrically-conductive circumferential portions, to the blockage. The method further includes, subsequently to advancing the shaft, selecting a subset of the electrically-conductive circumferential portions of the shaft for activation. The method further includes, subsequently to selecting the subset, applying a voltage between the selected subset of the electrically-conductive circumferential portions of the shaft and at least one reference electrode, such that the selected subset of the electrically-conductive circumferential portions attract the blockage. The method further includes, subsequently to beginning to apply the voltage, withdrawing the shaft from the body of the subject.

In some embodiments, the blockage is located within a blood vessel of the subject, and advancing the shaft includes advancing the shaft through vasculature of the subject.

In some embodiments, applying the voltage includes applying a positive unipolar voltage.

In some embodiments, selecting the subset includes:

acquiring an image of the blockage; and responsively to the image, selecting the subset.

In some embodiments, the electrically-conductive circumferential portions are first electrically-conductive circumferential portions, the shaft further includes multiple second electrically-conductive circumferential portions that are paired with the first electrically-conductive circumferential portions, respectively, such that the shaft includes multiple pairs of electrically-conductive circumferential portions, each pair including a respective one of the first electrically-conductive circumferential portions and a respective one of the second electrically-conductive circumferential portions, and selecting the subset includes:

measuring respective impedances between the pairs of electrically-conductive circumferential portions; and responsively to the measured impedances, selecting the subset.

The present invention will be more fully understood from the following detailed description of embodiments thereof, taken together with the drawings, in which:

DETAILED DESCRIPTION OF EMBODIMENTS

Overview

Figure 1:
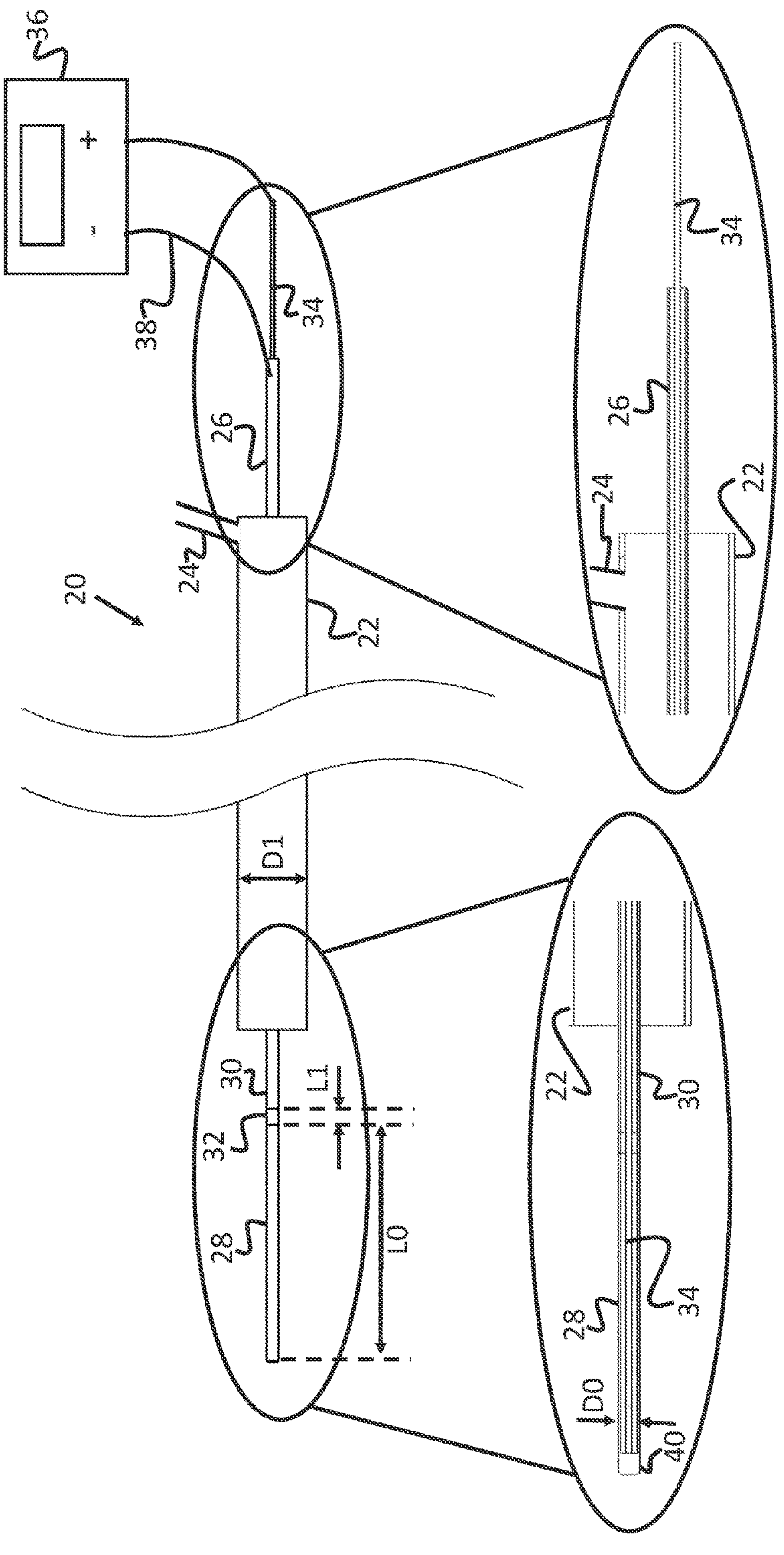
FIG. 1 is a schematic illustration of an apparatus for removing a thrombus from a body of a subject, in accordance with some embodiments of the present invention.

Embodiments of the present invention include various tubular thrombectomy devices for removing a thrombus from a blood vessel of a subject, by applying an electric field to the thrombus. Each of the devices comprises a shaft, which is typically hollow over all or most of its length. The shaft comprises at least one active electrode and at least one reference electrode. For example, the wall of the shaft may comprise two cylindrical (e.g., ring-shaped) electrically-conductive portions separated from one another by an electrically-insulative ring (or "spacer"). The active electrode is connected to one terminal of a power source, while the reference electrode is connected to another terminal of the power source.

The device is introduced into the subject's body, and is then advanced, typically under fluoroscopy, through the subject's vasculature, until the thrombus is reached. Subsequently, the active electrode is brought into contact with the thrombus, and a voltage is applied between the active electrode and the reference electrode. The applied voltage causes the active electrode to electrostatically attract the thrombus, such that the thrombus becomes ionically bonded (or "anchored") to the active electrode. Subsequently to applying the voltage, or while continuing to apply the voltage, the device and the thrombus are removed from the subject.

Typically, the applied voltage is a positive unipolar voltage. In the context of the present application, including the claims, a signal may be described as "positive unipolar" if the signal is positive for at least 80% of the duration of the signal.

In some embodiments, the device further comprises an aspiration tube, through which the shaft is configured to pass. Prior to applying the voltage, the aspiration tube is advanced to the thrombus, and the shaft is then advanced from the aspiration tube until the active electrode, which is typically disposed at or near the distal end of the shaft, is contained within the thrombus, or at least contacts the thrombus. Subsequently, the voltage is applied between the active electrode and the reference electrode, thus anchoring the thrombus to the active electrode. (Alternatively, the aspiration tube may be advanced over the shaft, before or after beginning to apply the voltage.) Following the anchoring of the thrombus, an aspirating device connected to the proximal end of the aspiration tube applies an axial suction force through the lumen of the tube. While the suction force is applied to the thrombus, the device is withdrawn from the subject.

Advantageously, the electrostatic and suction forces complement one another. If only the suction force were to be applied to the thrombus, the suction force might aspirate only the proximal portion of the thrombus, leaving the distal portion of the thrombus free to drift away from the aspiration tube, and possibly cause harm to the subject. Thus, by anchoring the thrombus to the shaft, the electrostatic force facilitates aspirating the entire thrombus. Conversely, if only the electrostatic force were to be applied, it might be difficult to keep the entire thrombus anchored to the shaft throughout the withdrawal of the device; the suction force thus facilitates the removal of the thrombus from the subject.

To increase the surface area over which the active electrode contacts the thrombus, and hence increase the electrostatic force that is applied to the thrombus, the diameter of the active electrode may be made greater than that of other portions of the shaft. The diameter of the other portions of the shaft, on the other hand, is generally kept relatively small, so as not to overly obstruct the lumen of the aspiration tube.

In other embodiments, the device does not comprise a separate aspiration tube. Rather, the shaft is open at its distal end, and has a relatively large diameter. Thus, while the shaft is withdrawn together with the thrombus, debris—including any fragments of the thrombus that break off during the withdrawal—may be aspirated through the open distal end of the shaft. Alternatively or additionally, other tools or agents—such as a stent, a net, a contrast agent, or a blood thinner—may be passed through the shaft and into the blood vessel, thus facilitating the removal of the thrombus. Alternatively or additionally, the shaft may be advanced over a guidewire. In some embodiments, the shaft is shaped to define multiple separate lumens, each of which may be used for aspiration and/or for any of the other functions described immediately above.

Typically, the respective wires that connect the electrodes to the power source are coiled along or within the wall of the shaft, such that the wires do not obstruct the lumen of the shaft.

In addition to facilitating the passage of debris and other items through the shaft, these embodiments provide a relatively large surface area for the active electrode, by virtue of the relatively large diameter of the shaft, and by virtue of the active electrode being part of the shaft wall. In contrast, were the active electrode passed through the lumen of an outer tube, the diameter of the active electrode might need to be more limited.

In some embodiments, the shaft comprises multiple active electrodes, along with one or more reference electrodes. (In some such embodiments, the diameter of the active electrodes is greater than that of the rest of shaft.) For example, the distal portion of the shaft may comprise two pairs of electrodes, each pair comprising an active electrode and a reference electrode separated from one another by an insulating spacer. Alternatively, the distal portion of the shaft may comprise a single reference electrode disposed between two active electrodes. As another alternative, the distal portion of the shaft may comprise multiple active electrodes, while the reference electrode, embodied by a tube or wire, may be disposed within the shaft.

Upon the shaft reaching the thrombus, the operating physician may activate multiple active electrodes simultaneously, such that electric current flows between multiple pairs of electrodes. Advantageously, by virtue of these multiple current pathways, a greater intensity of electric current (and hence a greater electrostatic force) may be applied to the thrombus, relative to if only a single pair of electrodes were to be activated. Alternatively or additionally, the active electrodes and/or the reference electrodes may be selectively activated, responsively to the location, size, and shape of the thrombus. For example, the physician may activate only those active electrodes that contact the thrombus, without activating any of the active electrodes that do not contact the thrombus. This selective activation may facilitate a more efficient application of electrostatic force, and/or reduce the risk to the subject.

In some embodiments, to facilitate the selective activation described above, the impedance between various pairs of electrodes may be measured, following the positioning of the electrodes at the thrombus. In general, the impedance of coagulated blood is higher than that of liquid blood. Hence, if a higher impedance is measured between a particular pair of electrodes, the pair may be activated; conversely, if a lower impedance is measured, the pair may not be activated. In some embodiments, to measure the impedance, an alternating current (having an amplitude that is typically less than 100 mA) is passed between the electrodes, and the voltage between the electrodes is measured. Alternatively, an alternating voltage (having an amplitude that is typically less than 100V) may be applied between the electrodes, and the current between the electrodes may be measured.

The scope of the present invention includes any suitable combination of the features described above. For example, a shaft comprising multiple active electrodes may be open at its distal end, or may be used together with an aspiration tube.

Although the present description refers mostly to a thrombus, it is noted that the devices described herein may be used to remove any type of blockage from a blood vessel, or any other duct (such as a gastrointestinal duct), within the body of a subject. Such a blockage may include, for example, coagulated blood, fat, cholesterol, plaque, any foreign material originating from outside the subject's body and having an inherent electric charge, or any combination of the above.

Combining Aspiration with Electrostatic Forces

Reference is initially made to FIG. 1, which is a schematic illustration of an apparatus 20 for removing a thrombus from a body of a subject, in accordance with some embodiments of the present invention. Enlarged cross-sections through the proximal and distal portions of apparatus are included in the inset portions of FIG. 1.

Apparatus 20 comprises an aspiration tube 22, which is configured to advance, through vasculature of the subject, to the thrombus. For example, if the thrombus is located in the middle cerebral artery (MCA), the tube may be inserted into the internal carotid artery (ICA), advanced through the ICA to the MCA, and then advanced through the MCA to the thrombus. Tube 22 comprises a proximal hub 24, which is configured to connect to a suction-applying device, such as a syringe or pump. Thus, a suction force generated by the suction-applying device may be applied, via the tube, to the thrombus. Typically, the inner diameter D1 of tube 22 is greater than 0.7 mm; this relatively large diameter facilitates using tube 22 for aspiration. (A microcatheter, on the other hand, typically has a much smaller diameter, e.g., a diameter that is less than 0.7 mm.)

Apparatus 20 further comprises a shaft 26, which is configured to pass through tube 22. Typically, shaft 26 is hollow over all or most of its length. Shaft 26 comprises two electrically-conductive circumferential portions: an active electrode 28, and a reference electrode 30. Active electrode 28 and reference electrode 30 are typically separated (and electrically insulated) from one another by an electrically-insulative circumferential portion of the shaft, referred to below as a "spacer" 32. (It is noted that the active electrode, reference electrode, and spacer 32 are described as being "circumferential" by virtue of lying along the circumference of the shaft.)

Typically, both tube 22 and shaft 26 are flexible, such as to facilitate navigating the shaft through the subject's vasculature.

In some embodiments, the shaft is configured to move axially through the tube. In other embodiments, the shaft is fixed to the inner wall of the tube, such that the active electrode protrudes from the distal end of the tube.

Active electrode 28 may comprise any suitable biocompatible conductive metal, such as gold, platinum, iridium, tungsten, an alloy of any of the above, and/or any other metal having a relatively high electronegativity. Typically, the active electrode is not expandable, i.e., the active electrode is configured to maintain a single shape. Typically, the length L0 of the active electrode is at least 5 mm, and/or the outer diameter DO of the active electrode is greater than 0.25 mm, e.g., greater than 0.5 mm. Advantageously, these dimensions provide a relatively large surface area for contacting the thrombus.

Likewise, reference electrode 30 may comprise any suitable biocompatible conductive metal; typically, however, the electronegativity of the reference electrode is less than that of the active electrode. Thus, for example, the reference electrode may comprise stainless steel, nitinol, and/or titanium. Typically, the reference electrode is not expandable, i.e., the reference electrode is configured to maintain a single shape.

In some embodiments, as illustrated in FIG. 1, each of the electrodes constitutes part of the wall of the shaft, i.e., the wall of the shaft comprises each of the electrodes. For example, each of the electrodes may comprise a tube or hollow cylinder (e.g., a ring) that is integral with the rest of the shaft wall. Alternatively, the more distal electrode—e.g., active electrode 28 in the case of FIG. 1—may comprise a solid disk or cylinder.

In other embodiments, at least one of the electrodes comprises a metallic structure, such as a tube, cylinder (e.g., a ring), coil, braid, or mesh, which is wrapped around the (electrically-insulative) wall of the shaft.

In some embodiments, at least one of the electrodes is radiopaque, to facilitate operating apparatus 20 under fluoroscopic guidance. Alternatively or additionally, one or more radiopaque markers may be coupled to at least one of the electrodes (e.g., to the distal end thereof), to any other portion of the shaft, and/or to any portion of the tube.

Spacer 32 typically comprises a biocompatible polymer, such as polyethylene terephthalate, polyimide, silicone, polyurethane, polyethylene, and/or polytetrafluoroethylene. Spacer 32 is typically ring-shaped. Typically, the length L1 of spacer 32 is less than 5 mm (e.g., less than 1 mm), such that less than 5 mm (e.g., less than 1 mm) separates the reference electrode from the active electrode.

Apparatus 20 further comprises a first electrically-conductive element 34, which is configured to connect the active electrode to a first terminal of a power source 36 (comprising, for example, a voltage source), and a second electrically-conductive element 38, which is configured to connect the reference electrode to a second terminal of power source 36. Each electrically-conductive element may comprise one or more straight or coiled wires, a tube that is proximally connected to a wire, and/or any other component. Each electrically-conductive element may comprise stainless steel, nitinol, titanium, and/or any other suitable conductive material.

Via first electrically-conductive element 34 and second electrically-conductive element 38, power source 36 applies a voltage between the active electrode and the reference electrode, thus anchoring the thrombus to the active electrode via ionic attraction. Typically, the voltage is positive over most or all of the duration for which the voltage is applied. (Hence, FIG. 1 labels the first terminal with a "+" sign, and the second terminal with a "−" sign.) Typically, for safety, the power source outputs less than 10 W, e.g., less than 1 W.

In some embodiments, as shown in FIG. 1, the active electrode is distal to the reference electrode; for example, the active electrode may be disposed at the distal end of the shaft. (Shaft 26 may comprise a conductive or insulative end cap 40, which is disposed distally to the active electrode.) First electrically-conductive element 34 runs through shaft 26 from the proximal end of the shaft to the active electrode, and is connected to the active electrode, e.g., at the distal end thereof.

In some such embodiments, as shown in FIG. 1, the reference electrode extends from spacer 32 to the proximal end of the shaft, such that second electrically-conductive element 38 may be disposed mostly or entirely externally to the shaft. In other such embodiments, the reference electrode does not extend to the proximal end of the shaft, and second electrically-conductive element 38 runs through shaft 26 from the proximal end of the shaft to the reference electrode. The portion of shaft 26 that is proximal to the reference electrode may comprise any suitable electrically-insulative material, such as any one or more of the polymers listed above.

In other embodiments, the active electrode is proximal to the reference electrode. Typically, in such embodiments, the active electrode does not extend to the proximal end of the shaft, and both the first electrically-conductive element and second electrically-conductive element run through the shaft. The portion of shaft 26 that is proximal to the active electrode may comprise any suitable electrically-insulative material, such as any of the polymers listed above.

Typically, for embodiments in which the reference electrode does not extend to the proximal end of the shaft, the surface area of the active electrode is greater than (e.g., at least twice or five times) the surface area of the reference electrode. Thus, typically, even if the thrombus contacts the reference electrode over the entire length of the reference electrode, a large majority (e.g., at least 80%) of the thrombus will nonetheless contact the active electrode, such that the attractive force applied to the thrombus by the active electrode will greatly exceed the repelling force applied by the reference electrode.

In yet other embodiments, the shaft comprises only a single electrically-conductive circumferential portion, which functions as the active electrode. Second electrically-conductive element 38, which passes through the shaft to the distal end of the shaft, functions as the reference electrode, e.g., as described below with reference to FIG. 6.

Tube 22 may comprise any suitable electrically-insulative material, such as any one or more of the polymers listed above. In general, the mechanical properties of the tube are similar to those of the shaft.

Figure 2A:
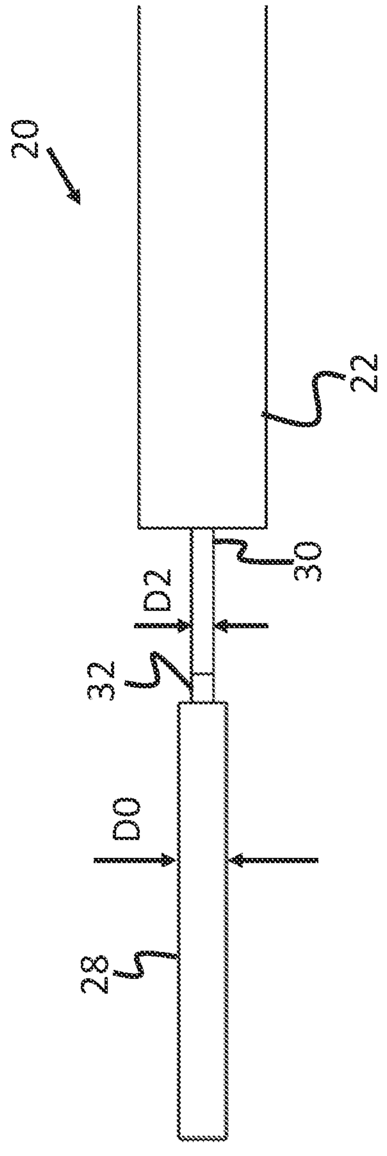
FIG. 2A is a schematic illustration of an apparatus comprising an enlarged active electrode, in accordance with some embodiments of the present invention.
Figure 2B:
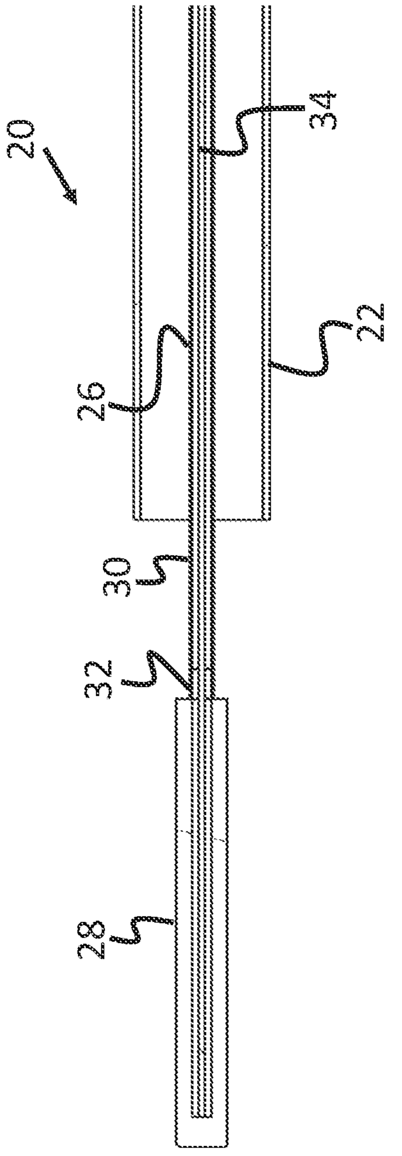
FIG. 2B schematically shows a cross-section through the apparatus shown in FIG. 2A, in accordance with some embodiments of the present invention.

Reference is now made to FIG. 2A, which is a schematic illustration of apparatus 20 comprising an enlarged active electrode, in accordance with some embodiments of the present invention. Reference is further made to FIG. 2B, which schematically shows a cross-section through apparatus 20 as shown in FIG. 2A, in accordance with some embodiments of the present invention.

In some embodiments, the active electrode is wider than the remainder of the shaft, i.e., diameter DO is greater than the maximum outer diameter D2 of the remainder of the shaft. For example, diameter DO may be at least 30% larger than, e.g., at least twice as large as, diameter D2. (Typically, in such embodiments, the active electrode is disposed at the distal end of the shaft, such that the diameter of the active electrode is greater than the diameter of any portion of the shaft that is proximal to the active electrode.) Advantageously, the wider active electrode provides an even greater surface area for contacting the thrombus.

Figure 3:
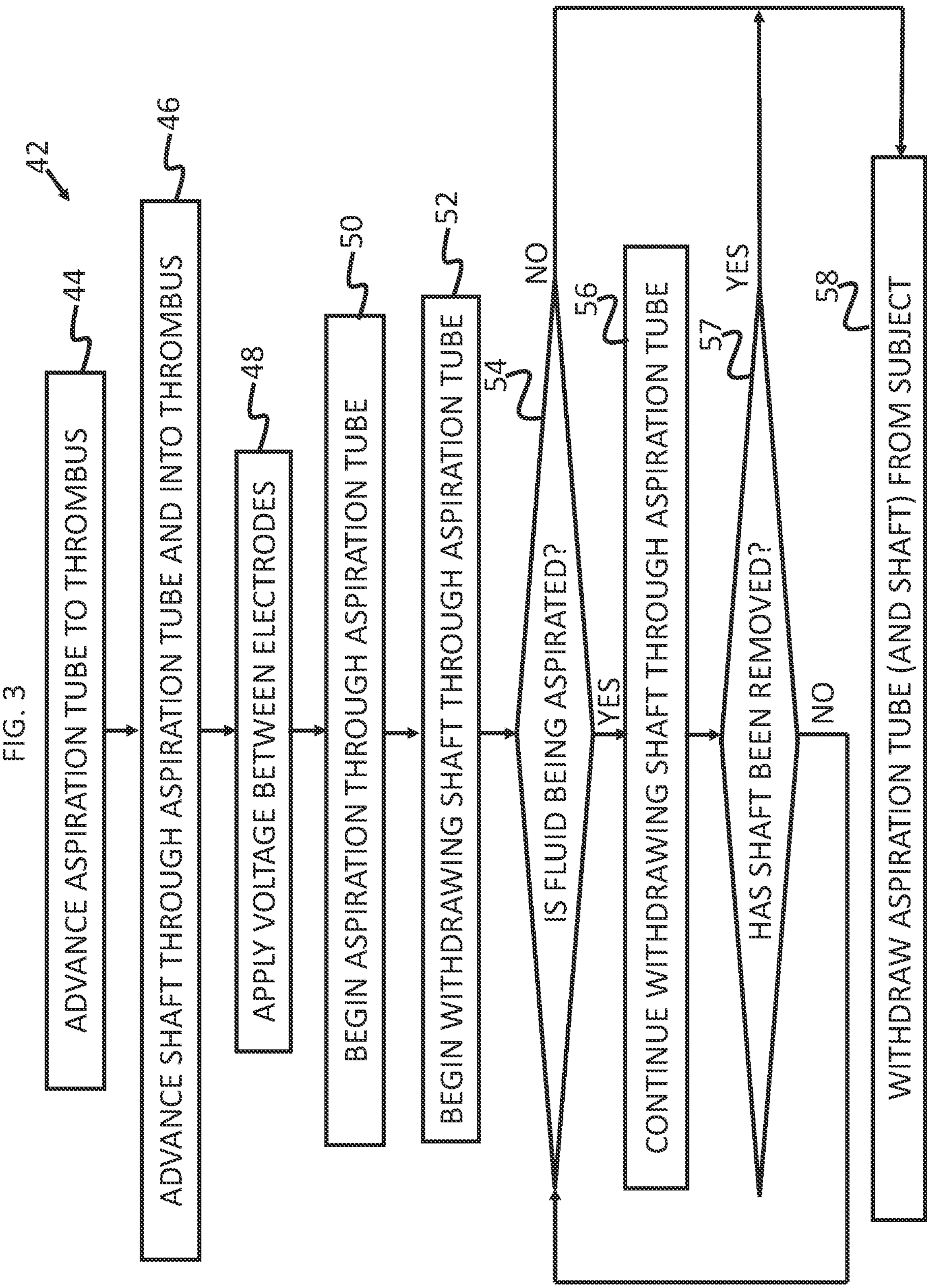
FIG. 3 is a flow diagram for a method for removing a thrombus from a body of a subject, in accordance with some embodiments of the present invention.

Reference is now made to FIG. 3, which is a flow diagram for a method 42 for removing a thrombus from a body of a subject using apparatus 20, in accordance with some embodiments of the present invention.

Method 42 begins with a tube-advancing step 44, at which the physician advances aspiration tube 22 to the thrombus. Typically, tube 22 is advanced over a guidewire, e.g., under fluoroscopic guidance. (The guidewire is typically passed through the thrombus.)

Subsequently, at a shaft-advancing step 46, shaft 26 is advanced through the aspiration tube and from the aspiration tube, such that active electrode 28 protrudes distally from the tube. (Typically, the shaft is advanced until the entire active electrode is outside of the tube.) For example, shaft 26 may be advanced from the aspiration tube until active electrode 28 is lodged within the thrombus. For embodiments in which the reference electrode is distal to the active electrode, shaft-advancing step 46 includes passing the shaft through the thrombus, such that the reference electrode is disposed distally to the thrombus. Typically, the shaft is advanced under fluoroscopic guidance.

Alternatively to advancing the tube before advancing the shaft, the shaft may be first advanced to, into, or through the thrombus, and the aspiration tube may then be advanced to the thrombus over the shaft. As yet another alternative, the tube and shaft may be advanced together, e.g., until the active electrode is lodged within the thrombus.

Subsequently to advancing the tube and the shaft, at a voltage-applying step 48, a voltage is applied between the active electrode and the reference electrode, such that the thrombus becomes anchored to the active electrode.

Subsequently to applying the voltage—or alternatively, while continuing to apply the voltage—a suitable suction-applying device applies a suction force, via the aspiration tube, to the thrombus. While the suction force is applied, the tube and the shaft are withdrawn from the body of the subject. Advantageously, by virtue of having applied (and/or continuing to apply) the voltage, the thrombus is anchored to the shaft while the suction force is applied.

For example, the application of the suction force may begin at an aspiration-beginning step 50. Subsequently to aspiration-beginning step 50, at a shaft-withdrawal-beginning step 52, the physician begins withdrawing the shaft through the aspiration tube. Next, the physician continually checks, at a first checking step 54, whether any fluid is being aspirated. As long as fluid is being aspirated, the physician continues withdrawing the shaft through the tube, at a shaft-withdrawal-continuing step 56, until the physician ascertains, at a second checking step 57, that the shaft has been removed from the tube. Subsequently, the physician withdraws the tube from the subject, at a withdrawing step 58.

Returning now to first checking step 54, if the physician ascertains, at any point in time, that no fluid is being aspirated, the physician assumes that the thrombus is blocking the distal end of the tube. Hence, the physician stops withdrawing the shaft through the tube, and then slowly withdraws both the shaft and the tube from the subject, at withdrawing step 58.

Using an Open Shaft

Figures 4A, 4B, 4C:
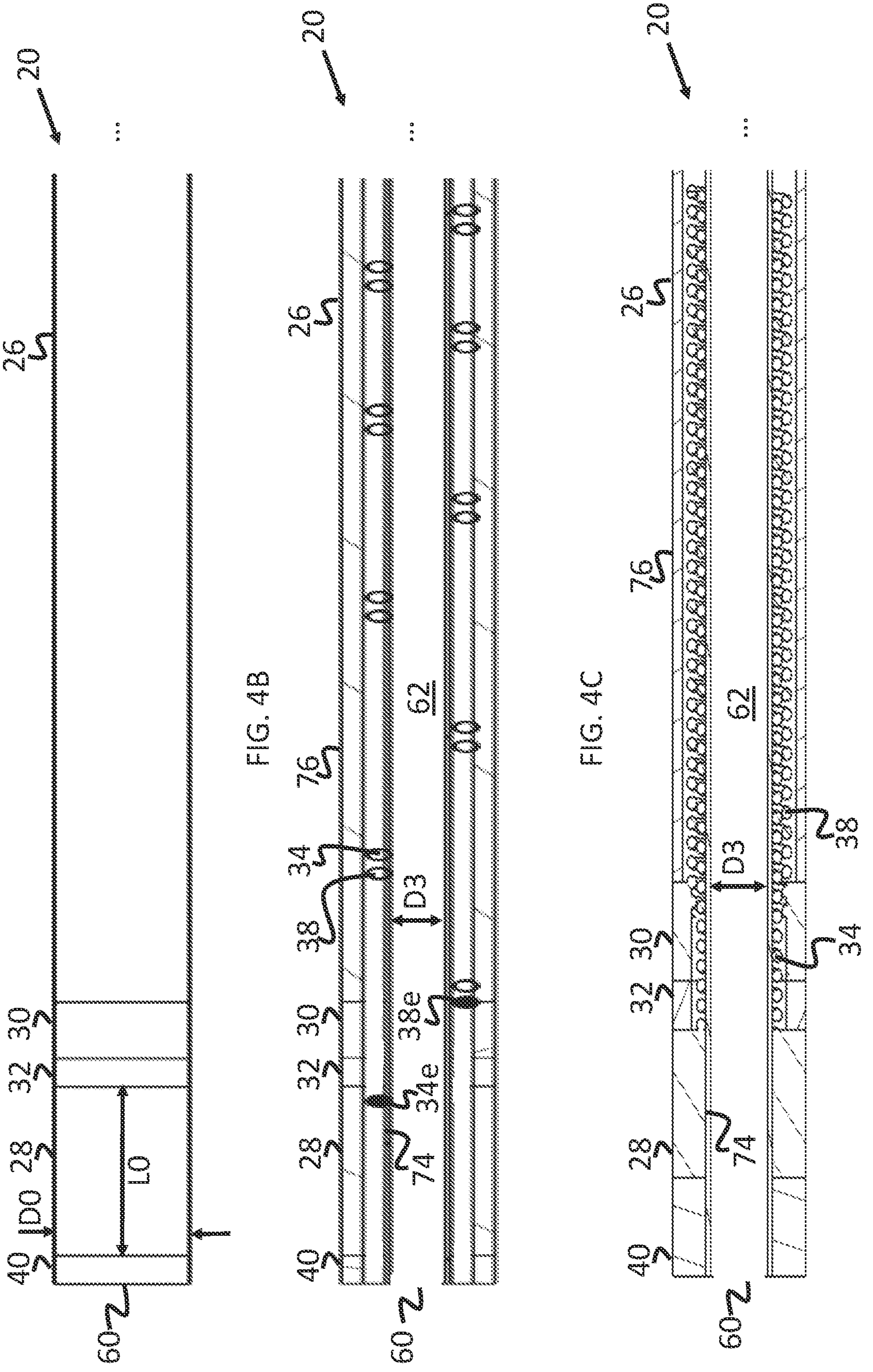
FIG. 4A is a schematic illustration of an apparatus comprising an open shaft, in accordance with some embodiments of the present invention.
FIG. 4B schematically shows a cross-section through the apparatus shown in FIG. 4A, in accordance with some embodiments of the present invention.
FIG. 4C schematically shows an alternate cross-section to the cross-section shown in FIG. 4B, in accordance with some embodiments of the present invention.

Reference is now made to FIG. 4A, which is a schematic illustration of apparatus 20 comprising an open shaft 26, in accordance with some embodiments of the present invention. Reference is further made to FIG. 4B, which schematically shows a cross-section through apparatus as shown in FIG. 4A, and to FIG. 4C, which schematically shows an alternate cross-section, in accordance with some embodiments of the present invention.

As shown in FIGS. 4A-C, in some embodiments, shaft 26 is hollow along its entire length, and has an open distal end 60, so as to facilitate the passage of tools and materials through the lumen 62 of the shaft. In such embodiments, the inner diameter D3 of the shaft—i.e., the diameter of lumen 62—is typically at least 0.3 mm, e.g., at least 0.5 mm. The shaft is thus able to accommodate a guidewire, the diameter of which is typically around 0.25 mm.

As in FIG. 1 and FIGS. 2A-B, shaft 26 comprises two electrically-conductive circumferential portions: active electrode 28 and reference electrode 30, each of which may comprise any of the (hollow) structures delineated above, such as a tube, cylinder (e.g., a ring), coil, or mesh. Reference electrode 30 may be disposed proximally or distally to active electrode 28.

Typically, length L0 of the active electrode is at least 5 mm, and/or outer diameter DO of the active electrode (which is typically the same as the outer diameter of the rest of the shaft) is at least 0.7 mm.

Typically, first electrically-conductive element 34 runs through the shaft from the proximal end of the shaft to the active electrode, thus connecting the active electrode to the power source. If the reference electrode extends to the proximal end of the shaft, the second electrically-conductive element may run externally to the shaft, as shown in FIG. 1. Typically, however, the reference electrode does not extend to the proximal end of the shaft, and second electrically-conductive element 38 also runs through the shaft, from the proximal end of the shaft to the reference electrode. In such embodiments, the surface area of the active electrode is typically greater than (e.g., at least twice or five times) the surface area of the reference electrode.

To reduce obstruction of lumen 62, first electrically-conductive element 34 and second electrically-conductive element 38 typically run along the inner wall 74 of the shaft, which faces lumen 62, or between inner wall 74 and the outer wall 76 of the shaft. (Equivalently, if the entire portion of the shaft that surrounds lumen 62 is referred to as the "wall" of the shaft, it may be said that the electrically-conductive elements run within the wall of the shaft.) For example, as shown in FIGS. 4B-C, the electrically-conductive elements may comprise respective coiled wires that run between the inner and outer walls of the shaft and connect to the two electrodes, respectively, at the respective distal ends 34*e* and 38*e* of the wires. Alternatively, one or both of the electrically-conductive elements may comprise an uncoiled wire, a tube, a braid, or a mesh that runs along inner wall 74 or between inner wall 74 and outer wall 76.

In some embodiments, as shown in FIG. 4B, the two electrically-conductive elements are disposed at the same radius from the center of the shaft. In other embodiments, as shown in FIG. 4C, the two electrically-conductive elements are disposed at different respective radii. In such embodiments, an insulating layer may separate the two electrically-conductive elements from one another. Alternatively, the two electrically-conductive elements may touch one another, but one or both of the two electrically-conductive elements may be covered by an electrically-insulative cover.

In some embodiments, apparatus 20 further comprises aspiration tube 22, as described above with reference to FIG. 1. Alternatively or additionally, shaft 26 may comprise a proximal hub, similar to proximal hub 24 (FIG. 1), such that the shaft may be used to aspirate debris (e.g., any thrombus fragments that break off) as the shaft and thrombus are withdrawn from the body.

For example, shaft 26 may be advanced to the thrombus, e.g., until active electrode 28 is lodged within the thrombus. Subsequently, a voltage between the electrodes may be applied. Subsequently to applying the voltage, or while continuing to apply the voltage, the shaft may be withdrawn, while debris is aspirated through distal end 60.

Alternatively or additionally, the shaft may be advanced over a guidewire, by first advancing the guidewire (e.g., under fluoroscopic guidance) to the thrombus, and then advancing the shaft over the guidewire. (The guidewire is typically passed through the thrombus.)

Alternatively or additionally, a tool, such as a net or stent, may be passed through distal end 60 and into the body of the subject, prior to or subsequently to beginning to apply the voltage between the electrodes. As the shaft and the tool are withdrawn from the subject, any fragments of the thrombus may be caught by the tool.

Alternatively or additionally, a contrast agent may be passed through distal end 60 and into the body of the subject, e.g., to help verify the location of the thrombus. Alternatively or additionally, a blood thinner may be passed through distal end 60 and into the body of the subject, e.g., to help treat any leftover fragments from the thrombus after the thrombus has been removed. Alternatively or additionally, a fluid, such as saline, may be passed through distal end 60 and into the body of the subject, e.g., to increase the pressure at the distal side of the thrombus, and thus help the removal of the thrombus.

Using Multiple Active Electrodes

Figure 5A:
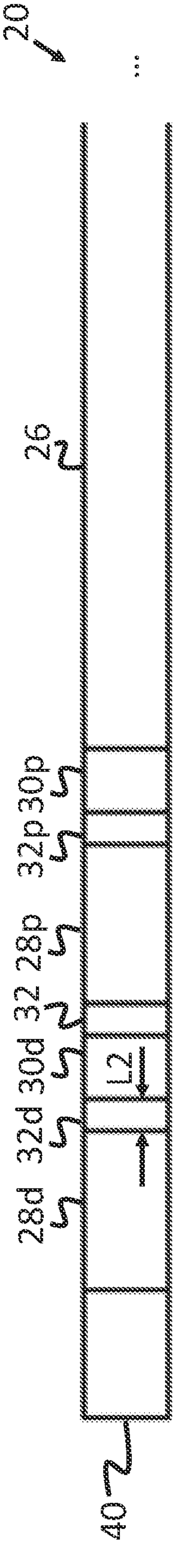
FIG. 5A is a schematic illustration of an apparatus comprising multiple active electrodes, in accordance with some embodiments of the present invention.
Figure 5B:
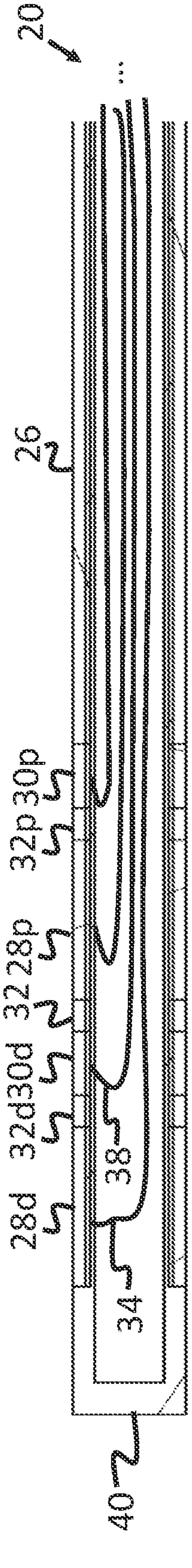
FIG. 5B schematically shows a cross-section through the apparatus shown in FIG. 5A, in accordance with some embodiments of the present invention.
Figure 5C:
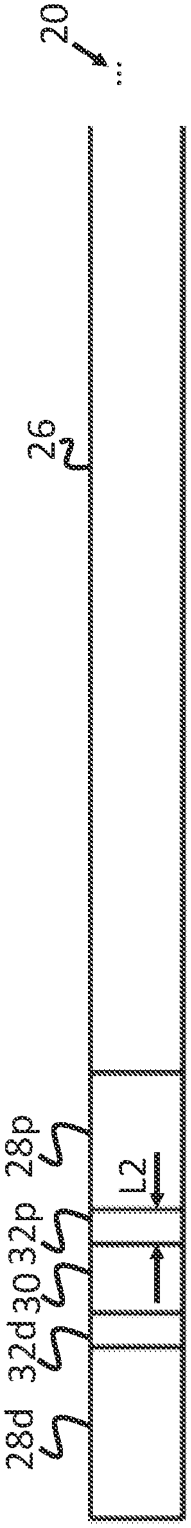
FIG. 5C is a schematic illustration of an apparatus comprising multiple active electrodes, in accordance with some embodiments of the present invention.

Reference is now made to FIGS. 5A and 5C, which are schematic illustrations of apparatus comprising multiple active electrodes, in accordance with some embodiments of the present invention. Reference is further made to FIG. 5B, which schematically shows a cross-section through apparatus 20 as shown in FIG. 5A, and to FIG. 5D, which schematically shows a cross-section through apparatus 20 as shown in FIG. 5C, in accordance with some embodiments of the present invention.

In some embodiments, shaft 26 comprises a plurality of active electrodes, along with one or more reference electrodes.

For example, as shown in FIGS. 5A-B, the shaft may comprise a distal pair of electrodes, comprising a distal active electrode 28*d* and a distal reference electrode 30*d*, and a more proximal pair of electrodes, disposed proximally to the distal pair, comprising a proximal active electrode 28*p* and a proximal reference electrode 30*p*. As further shown in FIGS. 5A-B, the distal electrodes may be separated (and electrically insulated) from one another by a distal spacer 32*d*, and the proximal electrodes may be separated from one another by a proximal spacer 32*p*. Yet another spacer 32 may separate (and electrically insulate) distal reference electrode 30*d* from proximal active electrode 28*p*.

In some embodiments, as shown in FIGS. 5A-B, each of the reference electrodes is disposed proximally to the active electrode with which the reference electrode is paired. In other embodiments, at least one of the reference electrodes is disposed distally to the active electrode with which the reference electrode is paired. In general, shaft 26 may comprise any suitable number of electrode pairs.

Figure 5D:
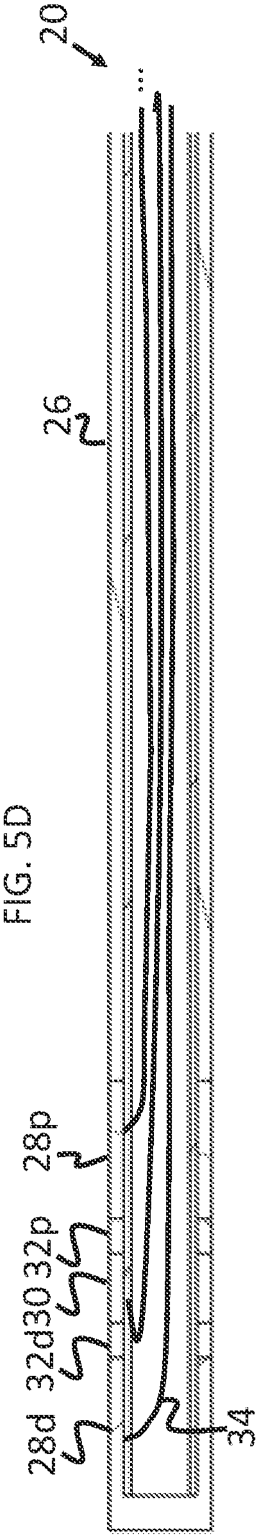
FIG. 5D schematically shows a cross-section through the apparatus shown in FIG. 5C, in accordance with some embodiments of the present invention.

Alternatively, as shown in FIGS. 5C-D, the shaft may comprise a triad of electrodes, comprising two active electrodes—in particular, a distal active electrode 28*d* and a proximal active electrode 28*p*—that are disposed distally and proximally, respectively, to a reference electrode 30. The distal and proximal active electrodes may be insulated from the reference electrode by a distal spacer 32*d* and a proximal spacer 32*p*, respectively.

Typically, the distance L2 between each active electrode the nearest reference electrode (which is typically equal to the length of the spacer that separates the two electrodes from one another) is less than 10 mm, e.g., less than 3 mm. By virtue of this small separation, the electric current that flows between the active electrode and the reference electrode passes through a relatively small portion of the subject's tissue. On the other hand, the distance between the active electrode and the next-nearest reference electrode (e.g., the distance between proximal active electrode 28*p* and distal reference electrode 30*d*) may be greater than L2. For example, this distance may be greater than 5 mm, e.g., greater than 10 mm. By virtue of this larger separation, a relatively small amount of current flows between different pairs or triads of electrodes.

Typically, the surface area of each active electrode is greater than (e.g., at least twice or five times) the surface area of each reference electrode. Thus, even if the thrombus contacts a reference electrode disposed between two active electrodes, the attractive force applied to the thrombus by the active electrodes may exceed the repelling force applied by the reference electrode.

It is noted that FIGS. 5C-D may be generalized in at least two ways. First, shaft 26 may comprise multiple triads of electrodes, successive triads being separated from each other by spacers 32. (Shaft 26 may thus comprise 2N active electrodes and N reference electrodes, for any suitable integer N.) Second, shaft 26 may comprise any suitable integer N of active electrodes, with N−1 reference electrodes disposed, respectively, between the successive pairs of active electrodes.

Figure 6:
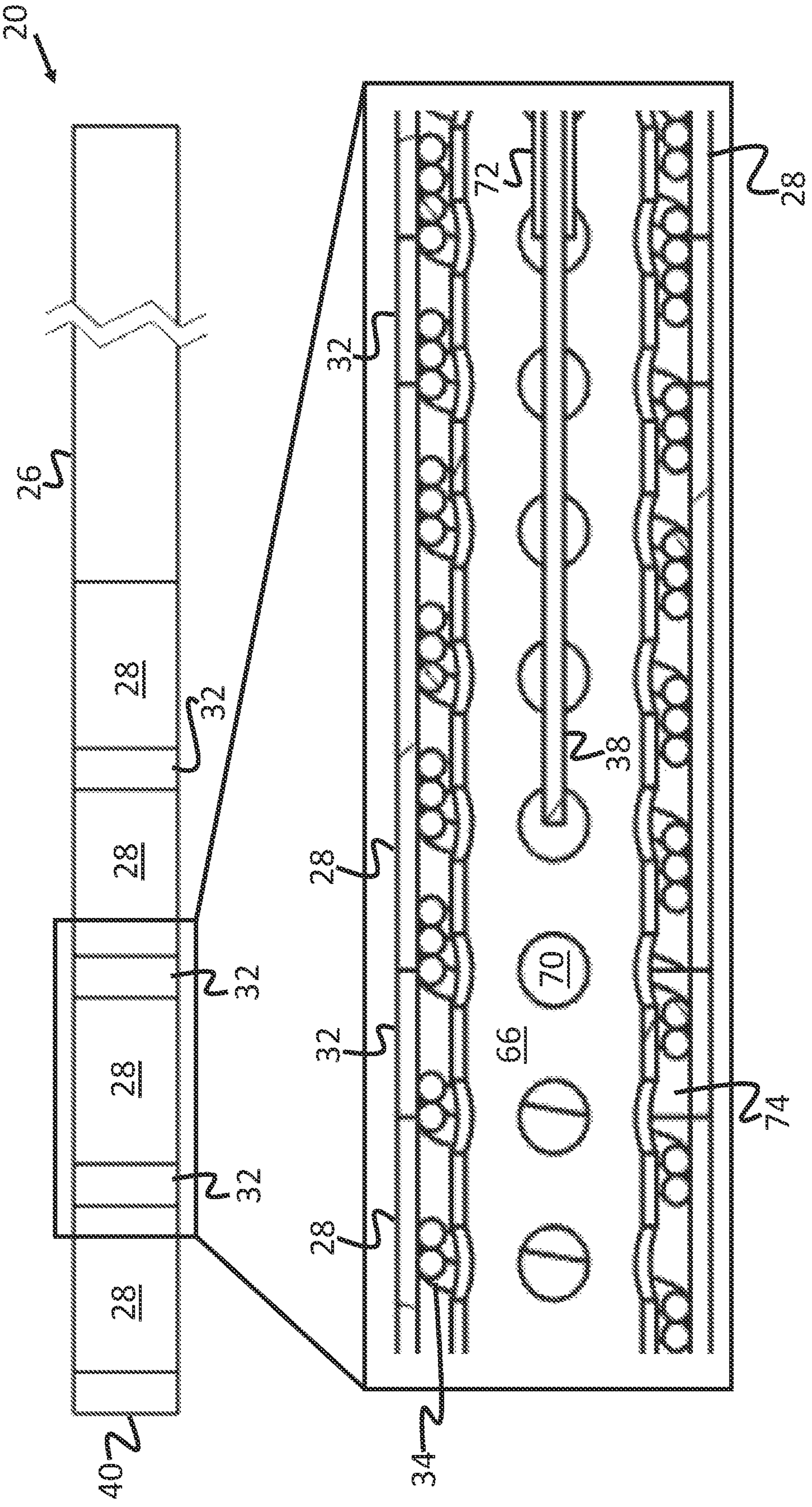
FIG. 6 is a schematic illustration of an apparatus comprising multiple active electrodes, in accordance with some embodiments of the present invention.

Reference is now made to FIG. 6, which is a schematic illustration of apparatus 20 comprising multiple active electrodes, in accordance with other embodiments of the present invention.

In some embodiments, apparatus 20 does not comprise any circumferential reference electrodes. Rather, second electrically-conductive element 38, which proximally connects to the second terminal of the power source and runs through the shaft from the proximal end of the shaft to the distal end of the shaft, functions as the reference electrode. Shaft 26 comprises multiple (e.g., 2-20, such as 3-8) circumferential active electrodes 28, separated from each other by spacers 32. (Typically, each spacer has a length of 0.1-5 mm, e.g., 0.4-1 mm.) Each active electrode is configured to attract the thrombus, when a voltage is applied between the active electrode and the reference electrode.

In such embodiments, shaft 26 typically comprises an electrically-insulative perforated layer (or "tube") 66, shaped to define a plurality of perforations 70, which is attached to inner wall 74 of the shaft. Upon activation of one or more of the active electrodes, electric current flows, via perforations 70, between the activated active electrodes and the reference electrode.

In some embodiments, perforated layer 66 extends through the entire shaft. In other embodiments, perforated layer 66 is disposed only at the more distal portion of the shaft that comprises active electrodes 28. Perforated layer 66 may comprise any suitable electrically-insulating material, such as any one or more of the polymers referred to above with reference to FIG. 1.

In some embodiments, the reference electrode is at least partly contained within an electrically-insulative sheath (or "cover") 72. In some embodiments, the reference electrode and sheath 72 are moveable with respect to one another. Thus, for example, prior to activating one or more of the active electrodes, the reference electrode may be advanced from sheath 72 (and/or the sheath may be withdrawn), such that the exposed distal portion of the reference electrode is positioned opposite the active electrodes that are to be activated. In other embodiments, the reference electrode and sheath are not moveable with respect to one another, such that the distal end of the reference electrode is permanently exposed. In such embodiments, the distal end of the reference electrode may be positioned opposite the active electrodes that are to be activated (or opposite all of the active electrodes, regardless of which electrodes are to be activated) by moving the sheath and reference electrode simultaneously.

Reference is again made to FIGS. 5A-D, in addition to FIG. 6.

Typically, one or more first electrically-conductive elements 34, which run through the shaft from the proximal end of the shaft to the active electrodes, connect the active electrodes to the first terminal of power source 36. In some embodiments, electrically-conductive elements 34 run along (e.g., are coiled along) inner wall 74. For example, for the embodiment of FIG. 6, electrically-conductive elements 34 may run between inner wall 74 and perforated layer 66.

Likewise, for FIGS. 5A-D, one or more second electrically-conductive elements 38, which run through the shaft from the proximal end of the shaft to the reference electrodes, connect the reference electrodes to the second terminal of the power source.

In general, the electrically-conductive elements may be isolated from each other by any suitable biocompatible insulating material, such as polyimide, silicone, polyurethane, or polyethylene.

In some embodiments, at least some (e.g., all) of the active electrodes are separately connected to the power source by multiple first electrically-conductive elements that run from the power source to these active electrodes, respectively. Likewise, for FIGS. 5A-D, at least some (e.g., all) of the reference electrodes may be separately connected to the second terminal of the power source by multiple second electrically-conductive elements 38.

In general, separately connecting the active electrodes to the power source allows the active electrodes to be separately activated. Thus, for example, subsequently to advancing the shaft to the thrombus, the physician may select a subset of the active electrodes for activation. For example, the physician may select at least one active electrode that contacts the thrombus or is at least opposite the thrombus, without selecting any of the other active electrodes. Subsequently to selecting the subset, the physician may activate the selected subset of the active electrodes, along with at least one of the reference electrodes, i.e., the physician may apply a voltage between the selected subset and at least one of the reference electrodes, without activating the other electrodes. (For example, with reference to FIGS. 5A-D, the physician may activate one pair or triad of electrodes without activating another pair or triad.) Advantageously, by activating only the selected subset of electrodes, the physician may reduce the amount of extraneous electric current that passes through the subject.

In some embodiments, the subset of electrodes is selected responsively to an acquired image of the thrombus. For example, subsequently to advancing shaft 26 to the thrombus, a contrast agent may be passed into the subject's body, in the vicinity of the thrombus. (For embodiments in which the distal end of the shaft is open, the contrast agent may be passed through the distal end of the shaft.) Subsequently, a fluoroscopic image, which shows the location of the thrombus relative to the active electrodes, may be acquired. Responsively to the position of the thrombus as shown in the image, the physician may select a subset of the active electrodes—and, if relevant, a subset of the reference electrodes—for activation. For example, the physician may select those active electrodes that contact the thrombus, without selecting any of the active electrodes that do not contact the thrombus.

Alternatively or additionally, the subset of electrodes may be selected responsively to measuring the impedance between various pairs of electrodes, by passing an alternating voltage or current between each of the pairs. As noted above in the Overview, a higher impedance may indicate the presence of the thrombus.

For example, for the embodiment shown in FIGS. 5A-B, the respective impedances between the distal and proximal pairs of electrodes may be measured. The pair for which the impedance is highest may then be selected for activation. Alternatively, both pairs may be selected, provided that the impedance seen for each of the pairs is greater than a particular threshold.

As another example, for the embodiments shown in FIGS. 5C-D and FIG. 6, the impedance may be measured between each of the active electrodes and the reference electrode. The active electrode that sees the higher impedance may then be selected for activation. Alternatively, each active electrode that sees an impedance that is greater than a particular threshold may be selected for activation.

Notwithstanding the above, at least some of the active electrodes may be electrically coupled (or "shorted") to each other, such that the electrodes are activated together. For example, a single electrically-conductive element may contact all of the active electrodes. Alternatively, apparatus 20 may comprise one or more interconnecting electrically-conductive elements (e.g., wires) that interconnect at least some of the active electrodes. As noted above in the Overview, such embodiments provide multiple simultaneous current pathways between the electrodes, such that the thrombus may be captured more effectively, relative to embodiments that comprise only a single active electrode.

For example, with reference to FIGS. 5C-D, for at least one of the triads, the proximal active electrode in the triad may be shorted to the distal active electrode in the triad, and/or to the distal active electrode in a neighboring triad.

Alternatively or additionally, for those embodiments that comprise multiple reference electrodes, at least some of the reference electrodes may be electrically coupled to each other.

In general, each of the circumferential electrodes may comprise any of the structures delineated above, such as a tube, cylinder (e.g., a ring), coil, or mesh. (The distalmost electrode may comprise a solid disk or cylinder.) The length and outer diameter of each active electrode may be as described above with reference to any of the earlier figures.

In general, each of the multiple-active-electrode embodiments described herein may be combined with any of the embodiments described with reference to the earlier figures. For example, a shaft comprising multiple active electrodes may be used with aspiration tube 22, as described above with reference to FIGS. 1 and 3, and/or may have an open distal end, and/or any of the other features described above with reference to FIGS. 4A-C, e.g., with respect to the manner in which the electrically-conductive elements, which connect the electrodes to the power source, run through the shaft.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for removing a blockage from a body of a subject, the apparatus comprising:

a tube, configured to advance to a guidewire;

a shaft being hollow and open at its distal end, the shaft configured to: pass through the tube, advance over the guidewire to the blockage, and to be withdrawn from the body of the subject, the shaft comprising:

one or more first electrodes, each of which constitutes part of a wall of the shaft or is wrapped around the wall; and one or more second electrodes, each of which constitutes part of the wall or is wrapped around the wall;

one or more first electrically-conductive elements, configured to connect the first electrodes to a first terminal of a power source; and one or more second electrically-conductive elements, configured to connect the second electrodes to a second terminal of the power source, each of the first electrodes being configured to attract the blockage when a voltage is applied by the power source, via one of the first electrically-conductive elements and one of the second electrically-conductive elements, between the first electrode and one of the second electrodes and after the tube and the shaft are advanced, such that the blockage is anchored to the shaft.

2. The apparatus according to claim 1, wherein the first electrically-conductive elements comprise multiple first electrically-conductive elements coupled, respectively, to at least some of the first electrodes, such that the first electrically-conductive elements are configured to connect the at least some of the first electrodes to the first terminal separately from each other.

3. The apparatus according to claim 1, further comprising one or more interconnecting electrically-conductive elements that interconnect at least some of the first electrodes.

4. The apparatus according to claim 1, wherein the shaft comprises:

a distal electrode pair, comprising one of the first electrodes and one of the second electrodes; and a more proximal electrode pair, which is disposed proximally to the distal electrode pair and comprises another one of the first electrodes and another one of the second electrodes.

5. The apparatus according to claim 4, wherein, in each of the distal electrode pair and the proximal electrode pair, the second electrode is disposed proximally to the first electrode.

6. The apparatus according to claim 1, wherein the second electrodes are disposed between successive pairs of the first electrodes, respectively.

7. The apparatus according to claim 1, wherein the shaft comprises at least one electrode triad comprising two of the first electrodes disposed distally and proximally, respectively, to one of the second electrodes.

8. The apparatus according to claim 1, wherein a distance between each of the first electrodes and a nearest one of the second electrodes is less than 10 mm.

9. The apparatus according to claim 8, wherein the distance is less than 3 mm.

10. The apparatus according to claim 1, wherein a distance between each of the first electrodes and a second-nearest one of the second electrodes is greater than 5 mm.

11. The apparatus according to claim 10, wherein the distance is greater than 10 mm.

12. The apparatus according to claim 1, wherein the shaft is fixed to an inner wall of the tube.

13. The apparatus according to claim 1, wherein the shaft is configured to move axially through the tube.

14. The apparatus according to claim 1, wherein an outer diameter of at least one of the first electrodes is greater than a maximum outer diameter of a remainder of the shaft.

15. The apparatus according to claim 1, wherein a surface area of each of the first electrodes is greater than that of each of the second electrodes.

16. A method for removing a blockage from a body of a subject, the method comprising:

advancing a tube to the blockage;

advancing a shaft over a guidewire to the blockage, the shaft being hollow and open at its distal end;

subsequently to advancing the tube and the shaft, applying a voltage between a first electrode, which constitutes part of a wall of the shaft or is wrapped around the wall, and which protrudes distally from the tube, and a second electrode, which constitutes part of the wall or is wrapped around the wall, such that the first electrode attracts the blockage, thereby causing the blockage to be anchored to the shaft; and subsequently to the blockage being anchored to the shaft, withdrawing the shaft from the body of the subject.

17. The method according to claim 16, wherein the method further comprises:

passing a tool through the open distal end of the shaft and into the body of the subject; and while withdrawing the shaft, withdrawing the tool while catching fragments of the blockage with the tool.

18. The method according to claim 16, wherein the method further comprises, while withdrawing the shaft, aspirating debris through the distal end of the shaft.

19. The method according to claim 16, wherein advancing a shaft over a guidewire comprises advancing the shaft through the tube such that the first electrode protrudes distally from the tube.

20. The method according to claim 16, wherein advancing a shaft over a guidewire comprises advancing the shaft until the first electrode is positioned within the blockage.

21. The method according to claim 16, wherein applying the voltage comprises applying a positive unipolar voltage.

22. The method according to claim 16, wherein advancing a shaft over a guidewire comprises advancing the shaft to move axially through the tube.

* * * * *